US00PP33610P2

(12) United States Plant Patent

Gitzels et al.

(10) Patent No.: US PP33,610 P2

(45) Date of Patent: Nov. 2, 2021

(54) *DAHLIA* PLANT NAMED 'BALDENIRE'

(50) Latin Name: *Dahlia variabilis*
Varietal Denomination: Baldenire

(71) Applicant: Ball Horticultural Company, West Chicago, IL (US)

(72) Inventors: Jeroen Gitzels, Zwaag (NL); Valentin Taquet, Amsterdam (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/334,321

(22) Filed: May 28, 2021

Related U.S. Application Data

(60) Provisional application No. 63/139,717, filed on Jan. 20, 2021.

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
CPC ..... A01H 6/144
See application file for complete search history.

(56) References Cited

PUBLICATIONS

UPOV hit on a *Dahlia* plant named, 'Baldenire', QZ PBR 20210212, filed Jan. 25, 2021.*
CPVO document, serial No. 20210212, filed Jan. 25, 2021, downloaded from https://online.plantvarieties.eu/publicConsultationDetails?registerId=20210212&denomination=baldenire&denominationFilter=contains.*

* cited by examiner

*Primary Examiner* — Anne Marie Grunberg
(74) *Attorney, Agent, or Firm* — Audrey Charles

(57) ABSTRACT

A new and distinct cultivar of *Dahlia* plant named 'Baldenire', characterized by its semi-double, anemone-type, light red and medium yellow colored inflorescences, dark green-colored foliage, and vigorous, upright-mounded growth habit, is disclosed.

1 Drawing Sheet

Latin name of genus and species of plant claimed: *Dahlia variabilis*.

Variety denomination: 'Baldenire'.

BACKGROUND OF THE INVENTION

The present invention relates to a new and distinct cultivar of *Dahlia* plant botanically known as *Dahlia variabilis* and hereinafter referred to by the cultivar name 'Baldenire'.

The new cultivar originated in a controlled breeding program in Hem, The Netherlands during August 2014. The objective of the breeding program was the development of *Dahlia* cultivars that are freely flowering with large inflorescences, mid-early season flower timing, and a vigorous, upright-mounded growth habit.

The new *Dahlia* cultivar is the result of open pollination. The female (seed) parent of the new cultivar is the proprietary *Dahlia variabilis* breeding selection coded E-243, not patented, characterized by its semi-double, anemone-type, light red-colored inflorescences, medium green-colored foliage, and moderately vigorous, upright-mounded growth habit. The male (pollen) parent of the new cultivar is unknown. The new cultivar was discovered as a single flowering plant within the progeny of the above stated open pollination during July 2015 in a controlled environment in Hem, The Netherlands.

Asexual reproduction of the new cultivar by terminal stem cuttings since July 2015 in Hem, The Netherlands and Andijk, The Netherlands has demonstrated that the new cultivar reproduces true-to-type with all the characteristics, as herein described, firmly fixed and retained through successive generations of such asexual propagation.

SUMMARY OF THE INVENTION

The following characteristics of the new cultivar have been repeatedly observed and can be used to distinguish 'Baldenire' as a new and distinct cultivar of *Dahlia* plant:

1. Semi-double, anemone-type, light red and medium yellow colored inflorescences;
2. Dark green-colored foliage; and
3. Vigorous, upright-mounded growth habit.

Plants of the new cultivar differ from plants of the female parent primarily in having bicolored inflorescences and increased growth vigor.

Of the many commercially available *Dahlia* cultivars, the most similar in comparison to the new cultivar is LABELLA 'Maggiore Fun Flame', not patented. However, in comparison, plants of the new cultivar differ from plants of 'Maggiore Fun Flame' in at least the following characteristics:

1. Plants of the new cultivar have a semi-double, anemone type inflorescence that is different from the double-type inflorescences of plants of 'Maggiore Fun Flame'; and
2. Plants of the new cultivar have a slightly darker shade of red-colored ray florets than plants of 'Maggiore Fun Flame'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldenire'. The 13-week-old plants were grown in 6.5-inch pots for 9 weeks in a glass-covered greenhouse in Hem, The Netherlands. Plants were given one pinch before transplant.

DETAILED BOTANICAL DESCRIPTION

Figure 1:
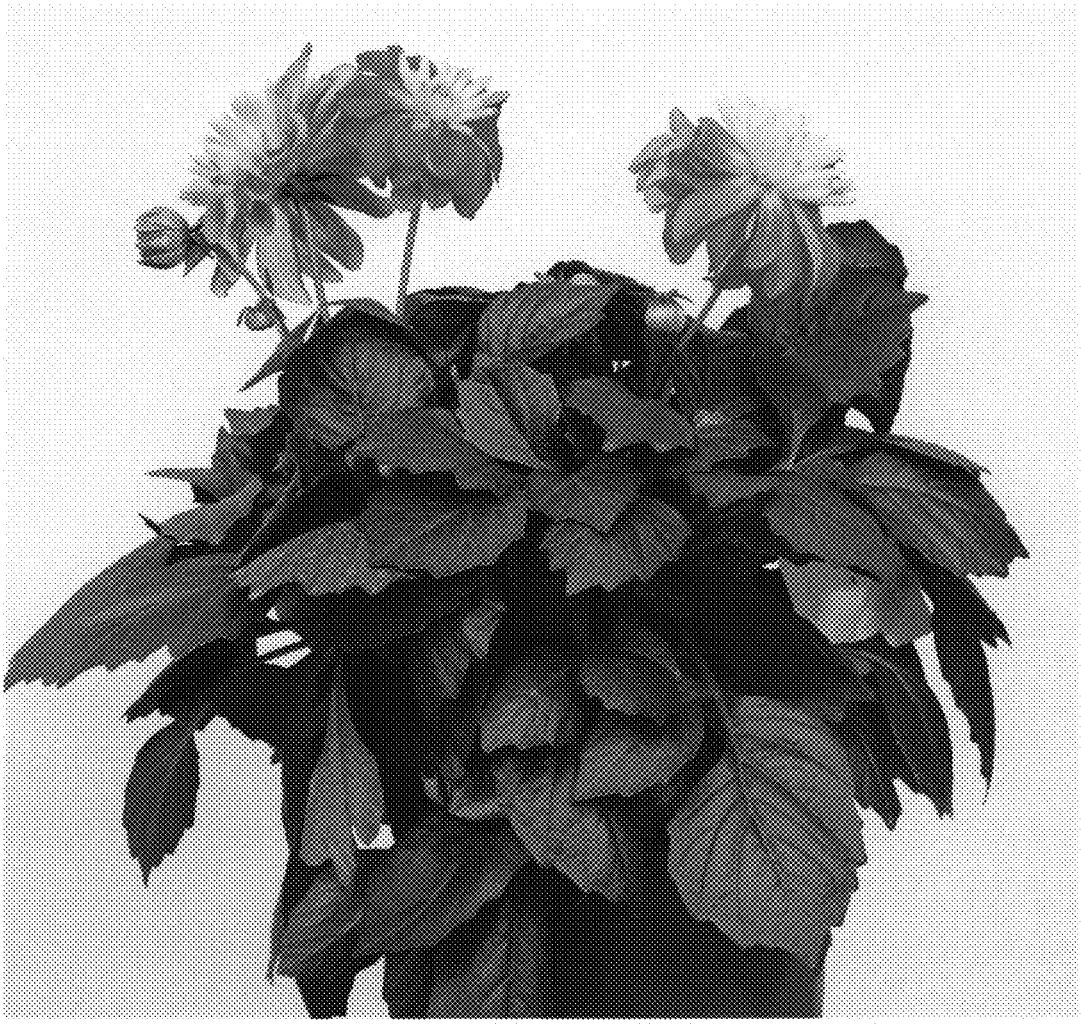
FIG. 1 illustrates a side view of the overall growth and flowering habit of 'Baldenire'.
Figure 2:
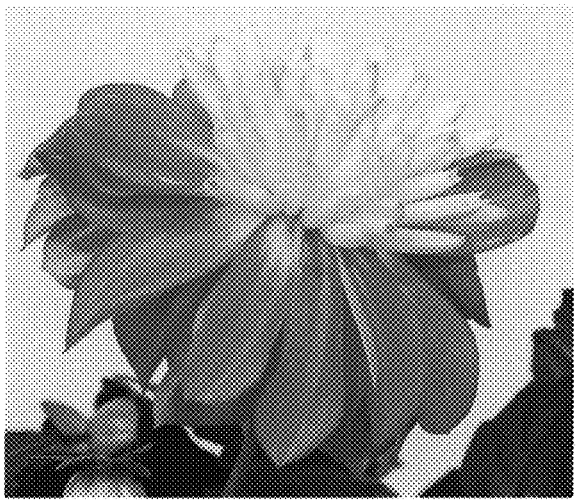
FIG. 2 illustrates a close-up view of an individual inflorescence of 'Baldenire'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2021 under natural light conditions in Boskoop, The Netherlands.

The following descriptions and measurements describe 13-week-old plants produced from cuttings from stock plants and grown in a glass-covered greenhouse under conditions comparable to those used in commercial practice. The plants were grown in Hem, The Netherlands in 6.5-inch pots for 9 weeks utilizing a soilless growth medium. Plants were given one pinch before transplant. Three Daminozide treatments were applied: one at 2,500 ppm two weeks after transplant, a second at 3,000 ppm four weeks after transplant and a third at 3,500 ppm six weeks after transplant. Greenhouse temperatures were maintained at an average of approximately 64° F. (18° C.) during the day and approximately 61° F. (16° C.) during the night. Supplemental lighting was used. Measurements and numerical values represent averages of typical plants.

Botanical classification: *Dahlia variabilis* 'Baldenire'.

Parentage:

*Female parent*.—Proprietary *Dahlia variabilis* breeding selection coded E-243, not patented.

*Male parent*.—Unknown.

Propagation:

*Type cutting*.—Terminal stem.

*Time to initiate roots*.—Approximately 9 to 12 days.

*Time to produce a rooted cutting*.—Approximately 21 to 28 days.

*Root description*.—Fine, fibrous.

*Rooting habit*.—Freely branching.

Plant description:

*Commercial crop time*.—Approximately 6 to 8 weeks from a rooted cutting to finish in a 15 cm pot.

*Growth habit and general appearance*.—Vigorous, upright-mounded.

*Size*.—Height from soil level to top of plant plane: Approximately 32.2 cm. Height from soil level to top of foliage: Approximately 23.9 cm. Width: Approximately 40.6 cm.

*Branch*.—Quantity of lateral branches per plant: Approximately 6. Strength: Moderately strong. Length of lateral branch: Approximately 15.6 cm. Diameter of lateral branch at central internode: Approximately 8.0 mm. Length of central internode of lateral branch: Approximately 2.5 cm. Texture: Glabrous. Color: 146A.

Foliage description:

*General description*.—Quantity of leaves per lateral branch: Approximately 14. Type: Simple and compound. Quantity of leaflets per compound leaf: Approximately 3, trifoliate. Fragrance: None detected. Arrangement: Opposite. Aspect: Petiole mostly perpendicular angle to stem with blade extending downward. Shape of leaf and leaflet: Ovate. Margin of leaf and leaflet: Widely serrate. Apex of leaf and leaflet: Acute. Base of leaf and leaflet: Broadly attenuate. Venation pattern: Pinnate.

*Simple leaf*.—Length: Approximately 12.4 cm. Width: Approximately 8.0 cm. Texture of upper surface: Glabrous. Texture of lower surface: Sparsely pubescent on venation. Color of upper surface: 139A blended with 147A. Color of lower surface: 191A to 191B. Length of petiole: Approximately 5.6 cm. Diameter of petiole: Approximately 3.5 mm. Texture of upper and lower surfaces of petiole: Glabrous. Color of upper surface of petiole: 146B with NN137B. Color of lower surface of petiole: 146B.

*Mature trifoliate leaf*.—Shape: Ovate in outline. Length of mature trifoliate leaf: Approximately 12.4 cm. Width of mature trifoliate leaf: Approximately 14.4 cm. Length of terminal leaflet: Approximately 10.8 cm. Width of terminal leaflet: Approximately 6.7 cm. Length of lateral leaflet: Approximately 7.9 cm. Width of lateral leaflet: Approximately 4.7 cm. Texture of upper and lower surfaces: Sparsely pubescent on venation. Color of upper surface: 139A blended with 147A. Color of lower surface: 191A and 191B. Length of petiole of mature trifoliate leaf: Approximately 5.0 cm. Diameter of petiole of mature trifoliate leaf: Approximately 3.5 mm. Texture of upper and lower surfaces of petiole: Glabrous. Color of upper surface of petiole: 146B with NN137B. Color of lower surface of petiole: 146B. Rachis: Not present.

Flowering description:

*Flowering habit*.—'Baldenire' is freely flowering under outdoor growing conditions with substantially continuous blooming from early summer through autumn.

*Lastingness of individual inflorescence on the plant*.—Approximately 2 weeks.

Inflorescence description:

*General description*.—Type: Semi-double, anemone-type, composite, consisting of multiple rows or ray florets, and disc florets, persistent. Aspect: Facing upward and moderately outward. Arrangement: Terminal, arising from leaf axils on strong peduncles positioned over the foliage. Disc and ray florets arranged acropetally on a capitulum. Quantity per plant: Approximately 3. Fragrance: None. Shape: Hemispherical when ray florets are fully open. Inflorescence diameter: Approximately 10.5 cm. Inflorescence depth: Approximately 6.9 cm. Disc diameter: Approximately 7.1 cm. Receptacle diameter at base: Approximately 8.0 cm. Receptacle depth: Approximately 2.0 mm. Receptacle color: 145B.

*Peduncle*.—Strength: Strong. Aspect: Erect. Length: Approximately 11.6 cm. Diameter: Approximately 3.0 mm. Texture: Glabrous. Color: 146A to 146B.

*Bud*.—Rate of bud opening: Generally takes 2 weeks for bud to progress from first color to fully open flower. Quantity per plant: Approximately 22.

*Bud just before opening*.—Shape: Oblate. Depth at first color: Approximately 9.0 mm. Diameter at first color: Approximately 1.3 cm. Texture: Glabrous. Color: Outer surface of the phyllaries 151C to 151D with base of 143C.

*Ray florets*.—Quantity per inflorescence: Approximately 32. Arrangement: Imbricate, in multiple whorls. Aspect: Slightly convex, slightly twisted. Shape: Obovate to elliptic. Margin: Entire. Apex: Apiculate. Base: Attenuate. Appearance: Matte. Length: Approximately 5.0 cm. Width: Approximately 2.5 cm. Texture of upper surface: Glabrous. Texture of lower surface: Sparsely pubescent on main veins, ribbed. Color of upper surface when first and fully open: 33A transitioning to N30A at apex with base of 1A to 1B. Color of lower surface when first and fully open: 30A to 30C with base of 2B and venation of 12C. Color of upper surface before senescence: 33B transitioning to 33A at apex with base of 1B. Color of lower surface before senescence: 30B to 30D with base of 2B and venation of 12C.

*Disc florets*.—Quantity per inflorescence: Approximately 65. Arrangement: Massed in center of inflorescence. Aspect: Erect. Shape: Tubular. Margin: Entire. Apex: 5 acute tips. Base: Fused. Length: Approximately 3.1 cm. Diameter at apex: Approximately 3.0 mm. Diameter at base: Approximately 2.0 mm. Texture: Glabrous. Color when fully open: 1A with base of 5A, heavily tinted with 30B to 30C before senescence.

*Outer phyllaries*.—Quantity: Approximately 5. Aspect: Flat, reflexed. Shape: Narrowly elliptic. Margin: Entire. Apex: Acute. Base: Truncate. Length: Approximately 1.8 cm. Width: Approximately 6.0 mm. Texture of upper and lower surfaces: Glabrous. Color of upper and lower surfaces: 137A.

*Inner phyllaries*.—Quantity: Approximately 1 per floret. Shape: Linear, imbricate. Margin: Entire. Apex: Broadly acute to obtuse. Base: Truncate. Length of outermost: Approximately 2.1 cm. Width of outermost: Approximately 8.0 mm. Length of innermost: Approximately 1.2 cm. Width of innermost: Approximately 5.0 mm. Texture of upper and lower surfaces: Glabrous. Color of upper and lower surfaces: 151D, translucent with 143A at base of outermost.

*Reproductive organs*.—Androecium: On disc florets. Stamen quantity: 5 per floret. Stamen length: Approximately 7.0 mm. Anther shape: Linear. Anther length: Approximately 2.0 mm. Anther color: 1B. Pollen amount: Sparse. Pollen color: 23A. Gynoecium: On disc florets. Pistil length: Approximately 1.0 cm. Stigma shape: 2 branched. Stigma length: Approximately 2.0 mm. Stigma width: Approximately 3.0 mm. Stigma color: 13B. Style length: Approximately 8.0 mm. Style color: 2B. Ovary length: Approximately 2.0 mm. Ovary color: 145C.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldenire', substantially as herein illustrated and described.

* * * * *